United States Patent
Hansen et al.

(10) Patent No.: US 11,992,592 B2
(45) Date of Patent: May 28, 2024

(54) MODULAR WARMING SYSTEM FOR DIALYSIS FLUID

(71) Applicant: Enthermics Medical Systems, Menomonee Falls, WI (US)

(72) Inventors: William J. Hansen, Pewaukee, WI (US); John Matthew Rotterman, Waynesville, OH (US)

(73) Assignee: Enthermics Medical Systems, Inc., Menomonee Falls, WI (US)

(*) Notice: Subject to any disclaimer, the term of this patent is extended or adjusted under 35 U.S.C. 154(b) by 861 days.

(21) Appl. No.: 16/519,406

(22) Filed: Jul. 23, 2019

(65) Prior Publication Data

US 2021/0023289 A1  Jan. 28, 2021

(51) Int. Cl.
*A61M 5/44* (2006.01)
*A61M 1/16* (2006.01)
*A61M 1/28* (2006.01)
*A61J 1/18* (2023.01)

(52) U.S. Cl.
CPC .............. *A61M 1/166* (2014.02); *A61M 1/28* (2013.01); *A61J 1/18* (2013.01); *A61M 2205/3368* (2013.01); *A61M 2205/36* (2013.01); *A61M 2205/587* (2013.01)

(58) Field of Classification Search
CPC ................ A61M 1/166; A61M 1/1664; A61M 2205/3368; A61M 5/44; A61M 5/445; A61M 2205/36; A61M 1/28; A61M 2209/08; A61M 2209/084; A61B 2050/001; A61B 2050/0016; A61B 2050/0018; A61J 2200/70; A61J 2200/72; F24F 2006/008; F24F 11/523
See application file for complete search history.

(56) References Cited

U.S. PATENT DOCUMENTS

| | | | | |
|---|---|---|---|---|
| 3,736,981 | A | * 6/1973 | Shevlin | F24C 15/166 99/359 |
| 5,176,343 | A | * 1/1993 | Cheney, II | H01R 13/60 248/51 |
| 5,474,683 | A | 12/1995 | Bryant et al. | |

(Continued)

OTHER PUBLICATIONS

FloorMount iv fluid warmer, Smithworks Medical Inc, website snapshot taken Jun. 10, 2016, accessed on Nov. 22, 2022 using The Wayback Machine (Year: 2016).*

*Primary Examiner* — Phillip A Gray
*Assistant Examiner* — Anna E Goldberg-Richmeier
(74) *Attorney, Agent, or Firm* — Boyle Fredrickson S.C.

(57) ABSTRACT

An extremely lightweight and compact heating system greatly increasing patient mobility is provided. The use of a flat plate can be used to greatly decrease package size and weight while providing comparable heat transfer by exploiting the ability of the dialysis bags to conform to this surface and through the greater heating area possible with the flat plate design. A short rim around the plate provides centering and protecting against minor leakage without substantially increasing package height. Protection against leakage is buttressed by sealing the rim to the plate and the use of 12 V only within the heating unit. The result is a lightweight warming device with a short that can be easily transported by the patient greatly improving patient lifestyle and freedom.

20 Claims, 4 Drawing Sheets

(56) References Cited

U.S. PATENT DOCUMENTS

| | | | | |
|---|---|---|---|---|
| 6,142,974 | A * | 11/2000 | Kistner | F28D 7/0066 604/113 |
| 7,238,170 | B2 * | 7/2007 | Park | A61F 7/0085 604/113 |
| 2006/0291533 | A1 * | 12/2006 | Faries, Jr. | A61J 1/1462 374/E11.018 |
| 2009/0088709 | A1 * | 4/2009 | Salvadori | A61F 5/4404 604/317 |
| 2010/0059498 | A1 * | 3/2010 | Hansen | A61M 5/445 219/400 |
| 2014/0199057 | A1 * | 7/2014 | Hansen | A61M 1/1664 392/443 |
| 2014/0231406 | A1 * | 8/2014 | Tsang | A61M 5/44 219/394 |
| 2015/0308732 | A1 * | 10/2015 | Lee | F25D 21/14 62/291 |
| 2017/0128653 | A1 * | 5/2017 | Yuds | A61M 1/14 |
| 2017/0281879 | A1 * | 10/2017 | Shimel | G05D 23/1931 |
| 2019/0261813 | A1 * | 8/2019 | Russier | A47J 36/321 |
| 2020/0214360 | A1 * | 7/2020 | Nguyen | A24F 40/40 |
| 2020/0261638 | A1 * | 8/2020 | Lindo | H05B 3/34 |

* cited by examiner

MODULAR WARMING SYSTEM FOR DIALYSIS FLUID

BACKGROUND OF THE INVENTION

The present invention relates to warming systems for medical fluids and in particular to a warming system adapted to support large fluid volumes used in peritoneal dialysis.

Peritoneal dialysis is often used in the treatment of patients with severe kidney disease as an alternative to hemodialysis. While hemodialysis removes waste and excess water from the blood using an external semipermeable membrane as a substitute for the kidney, peritoneal dialysis uses for this purpose the patient's peritoneum membrane that lines the abdominal cavity. Generally, a large quantity of sterile fluid is introduced into the abdomen (approximately 5 liters) where it resides to collect waste products from the proximate blood vessels. The water is then withdrawn bringing with it waste products. This process is repeated on a regular basis.

Infusing the large amount of dialysate needed for this procedure can uncomfortably change the core temperature of the patient, particularly when the dialysate is at room temperature, substantially below normal body core temperatures. For this reason, it is known to provide heaters for heating the dialysis fluid prior to use, for example, as taught by US patent application 2014/0199057 entitled "Warming System for Dialysis Fluid" assigned to the present assignee and hereby incorporated by reference. Such heaters provide an upwardly curved metallic basin to maximize contact between the large dialysis bags and high wattage heaters connected to the line power to minimize, to the extent possible, the time required to bring the liquid up to temperature.

SUMMARY OF THE INVENTION

The present inventors have recognized that existing heaters present a substantial impediment to mobility by patients who require multiple infusions on a daily basis. Accordingly, the present invention provides extremely lightweight and compact heating system greatly increasing patient mobility. In particular, the inventors have determined that the use of a flat plate instead of metallic basin can be used to greatly decrease package size and weight while providing comparable heat transfer by exploiting the ability of the dialysis bags to conform to this surface and through the greater heating area possible with the flat plate design. A short rim around the plate provides centering and protection against minor leakage without substantially increasing package height. Protection against leakage is buttressed by sealing the rim to the plate and the use of 12 V only within the heating unit. The result is a lightweight warming device with a short profile that can be easily transported by the patient greatly improving patient lifestyle and freedom Specifically the invention provides, in one embodiment, a warming module for infusible liquids including an upwardly exposed planar metal warming plate sized to receive a flexible polymer bag holding the infusible liquid; a polymer housing supporting the warming plate and providing an upwardly extending peripheral ridge presenting a sealed continuous surface between the housing and the warming plate; and a heater element attached to the warming plate to conduct heat through the warming plate and bag into the contained infusible liquid when the bag is held on the warming plate.

It is thus one feature of at least one embodiment of the invention to provide an extremely low profile heater for large peritoneal dialysis bags permitting improved patient mobility.

The rim may have a height of less than 2 cm.

It is thus one feature of at least one embodiment of the invention to limit the rim height by recognizing that leakage containment is limited by the depth of any hand openings otherwise necessary to help place and remove the dialysis bag. By simply limiting the rim height, hand openings can also be eliminated.

The rim may extend upward from the edges of the plate by an angle of less than 45°.

It is thus one feature of at least one embodiment of the invention to permit the bag to conform as closely as possible to the metal plate over the greatest area.

The heater may be attached to cover at least 90% of the plate area.

It is thus one feature of at least one embodiment of the invention to offset curved walls of the heating plate through the use of greater heating plate to heater contact area.

The warming module may further include a heater and heater control circuitry and a remote wall adapter providing a voltage less than or equal to 12 V to the heater and heater control circuitry from the remote wall adapter through an adapter cord.

It is thus a feature of at least one embodiment of the invention to reduce the risks from bag failure when there is a reduced rim height by limiting internal voltages provided to the heater.

The warming module may be less than five pounds.

It is thus one feature of at least one embodiment of the invention to provide a warming system that can be easily transported for example during travel on an aircraft or automobile.

The rim may include at least one proximity sensor detecting the presence of the IV bag on the plate to control the heater. At least two proximity sensors may be displaced laterally from each other. The at least two proximity sensors may be displaced apart by at least 10 cm.

It is thus one feature of at least one embodiment of the invention to provide a warming system that indicates misalignment of the bag on the heating plate not just placement of the bag on the warming plate. The use of more than one sensor can also be used as backup should there be sensor failure.

The rim may include at least one visual indicator indicating a warming state of the flexible polymer bag holding the infusible liquid. The at least one light indicator may be at least one light emitting diode bulb positioned beneath a light diffuser.

It is thus one feature of at least one embodiment of the invention to provide a warming system that provides quick visual indication of fluid warming status that may be used by the visually impaired and provides convenience in a hectic environment such as in a hospital emergency room where audio alerts and small display screens are difficult to observe.

The light emitting diode and light diffuser may be arranged around a perimeter of the housing. The at least one light emitting diode and light diffuser may be arranged on the angled rim.

It is thus one feature of at least one embodiment of the invention to superimpose the warming state onto the heated bag so that the user is quickly guided to the heated bag, for example, among multiple bags in a warming system.

The light indicator may present a warming state indicating that the bag is warming and is not at a predetermined temperature or is warmed to a predetermined temperature by means of a first color indicating that the bag is warming and a second color indicating that the bag is warmed to the predetermined temperature.

The light indicator may present a warming state indicating that the bag is warming and is not at a predetermined temperature or is warmed to a predetermined temperature by means of changing an intensity of the light.

In another embodiment, a warming system for infusible liquids includes at least two warming modules arranged in a stacked configuration along an axis extending along a height of each warming module, each warming module having an upwardly exposed planar metal warming plate sized to receive a flexible polymer bag holding the infusible liquid; a polymer housing supporting the warming plate and providing an upwardly extending peripheral rim presenting a sealed continuous surface between the housing and the warming plate; and a heater element attached to the warming plate to conduct heat through the warming plate and bag into the contained infusible liquid when the bag is held on the warming plate.

It is thus one feature of at least one embodiment of the invention to provide a warming system that warms multiple dialysis bags at once, speeding up waiting times.

The system may further include a mounting bracket having a first plate configured to be attached to the housing and a second plate extending perpendicular to the first plate and configured to be attached to a support element.

It is thus one feature of at least one embodiment of the invention to provide a warming system that allows each modular unit to be easily interchanged or replaced for repair.

A spacing between the at least two warming modules may be less than 15 cm. A spacing between the at least two warming modules is less than two times a height of the dialysis bag repose on the warming plate.

It is thus one feature of at least one embodiment of the invention to provide a warming system that maximizes vertical space by efficiently stacking modular units on the multi-unit warming system with minimized space between modules.

These particular features and advantages may apply to only some embodiments falling within the claims and thus do not define the scope of the invention.

DETAILED DESCRIPTION OF THE PREFERRED EMBODIMENT

Figure 1:
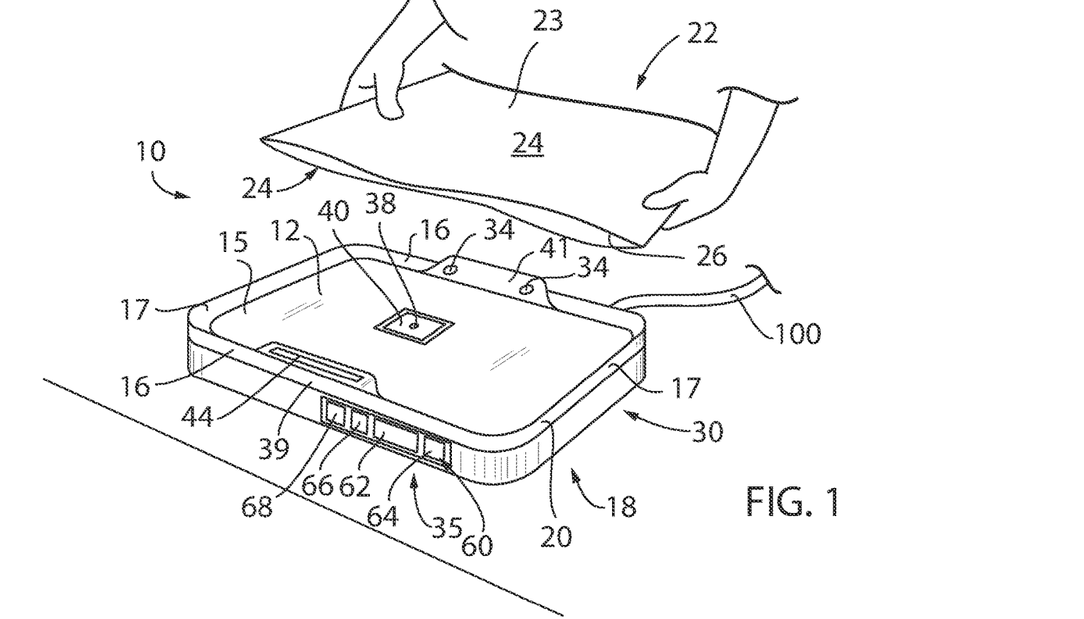
FIG. 1 is a front perspective view taken from above of a warming module of the present invention showing an upwardly open warming plate for receiving a bag of sterile dialysate and placed on the warming plate with a user's hands.

Referring now to FIG. 1, a warming unit 10 of the present invention may provide for an upwardly exposed warming plate 12 having a generally rectangular, planar support surface. An outer edge 15 of the warming plate 12 joins with upwardly sloping opposed sidewalls 16 and opposed end walls 17 of an upwardly extending peripheral upper rim 20 of housing 18 supporting the warming plate 12 at an open top end. The housing 18 provides a continuous watertight surface between its upwardly sloping opposed sidewalls 16 and opposed end walls 17 and the warming plate 12. Generally, the warming plate 12 will be fabricated from a conductive metal such as aluminum or anodized aluminum to provide a heat spreading feature as will be described below.

Figure 2:
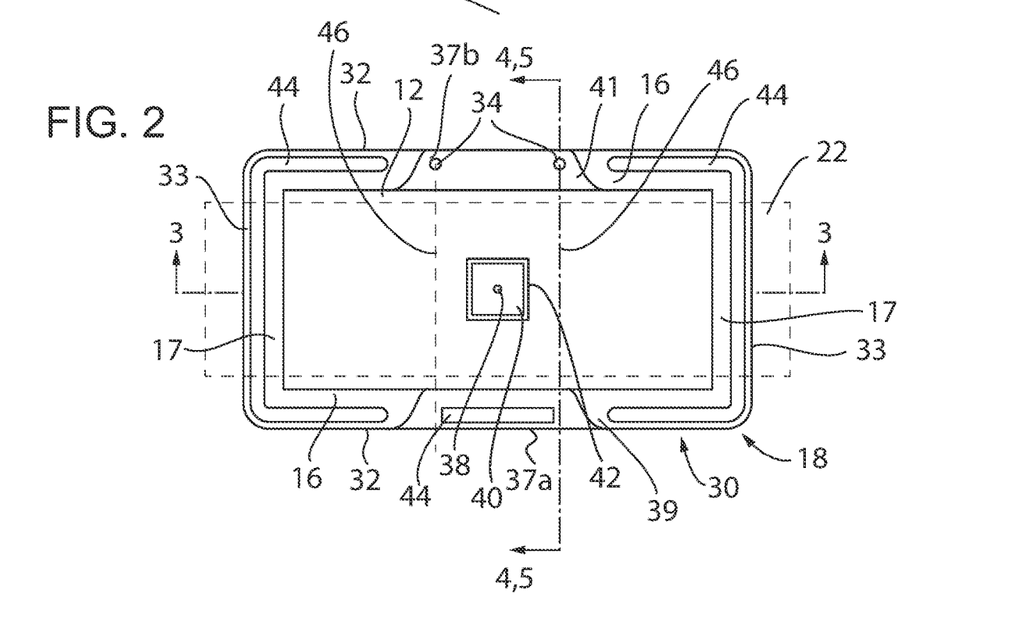
FIG. 2 is a top plan view of the warming module of FIG. 1 showing positioning of light indicators on an outer perimeter of the warming plate to visibly indicate a heating status of the bag to the user.

Referring also to FIG. 2, the warming plate 12 is sized to receive and substantially fully support a dialysis bag 22 holding, for example, five liters of infusion liquid 23. The infusion liquid 23 may, for example, be a saline solution for peritoneal dialysis. The warming plate 12 may have an area of at least 35 cm length and at least 25 cm width to support the dialysis bag 22 thereon.

As is understood in the art, the dialysis bag 22 may be constructed of a flexible transparent plastic material, such as a vinyl, and fabricated by joining two sheets 24 of the material at a peripheral seam 26 to provide within the seam 26 an enclosed pocket into which sterile infusion liquid 23 may be held.

The flexible material of the dialysis bag 22 permits the dialysis bag 22 to adopt a variety of different volumetric configurations and the flat warming plate 12 is designed to maximize heat transfer to the contained infusion liquid 23. In particular, the flat warming plate 12 is shaped to support the dialysis bag 22 with one lower sheet 24 of the dialysis bag 22 lying in close abutment to the warming plate 12 so that the seams 26 between the sheets 24 lie generally along a horizontal plane displaced close to the warming plate 12. In this way, contact between the dialysis bag 22 and the planar warming plate 12 may be substantially maximized and the thermal path to any volume element of the infusion liquid 23 from the warming plate 12 reduced.

Figure 3:
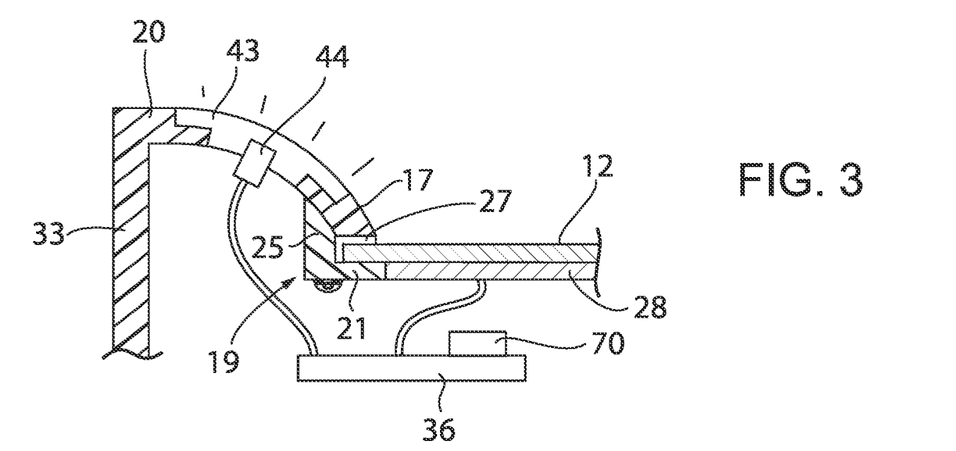
FIG. 3 is a fragmentary cross-section along line 3-3 of FIG. 2 showing attachment of the housing to the outer surface of the warming plate and light indicators positioned on a sloped surface of the inner opening of the housing.

Referring also to FIG. 3, a heater 28 may be attached to an underside of the warming plate 12 to conduct heat directly into the supported dialysis bag 22. The heater 28 may be substantially continuous over the warming plate 12 except for a small opening for a thermal sensor as will be described below. Generally, the heater 28 contacts the warming plate 12 over substantially an entire area of the warming plate 12 so that a low temperature (gentle) heat implemented over the portions of the warming plate 12 contacting the dialysis bag 22 rapidly heat the contained infusion liquid 23 without large temperature differences. For this purpose, the area of the heater 28 will typically be greater than 50 square inches and preferably greater than 100 square inches or more. The area of the heater 28 may cover an area of at least 80% and at least 90% and at least 95% of a lower surface of the warming plate 12 therefore maximizing direct contact between the heater 28 and the warming plate 12 to be at least and generally greater than the amount that would be provided by a curved metal basin where the edges of the basin do not contact the heater 28.

A suitable heater 28 may be a silicone rubber electric heater. As is understood in the art, a silicone rubber electric heater provides a resistive conductive element, for example an etched foil or wire, embedded in a silicone rubber mat and is broadly commercially available from multiple vendors.

Figures 8, 9, 10, 11:
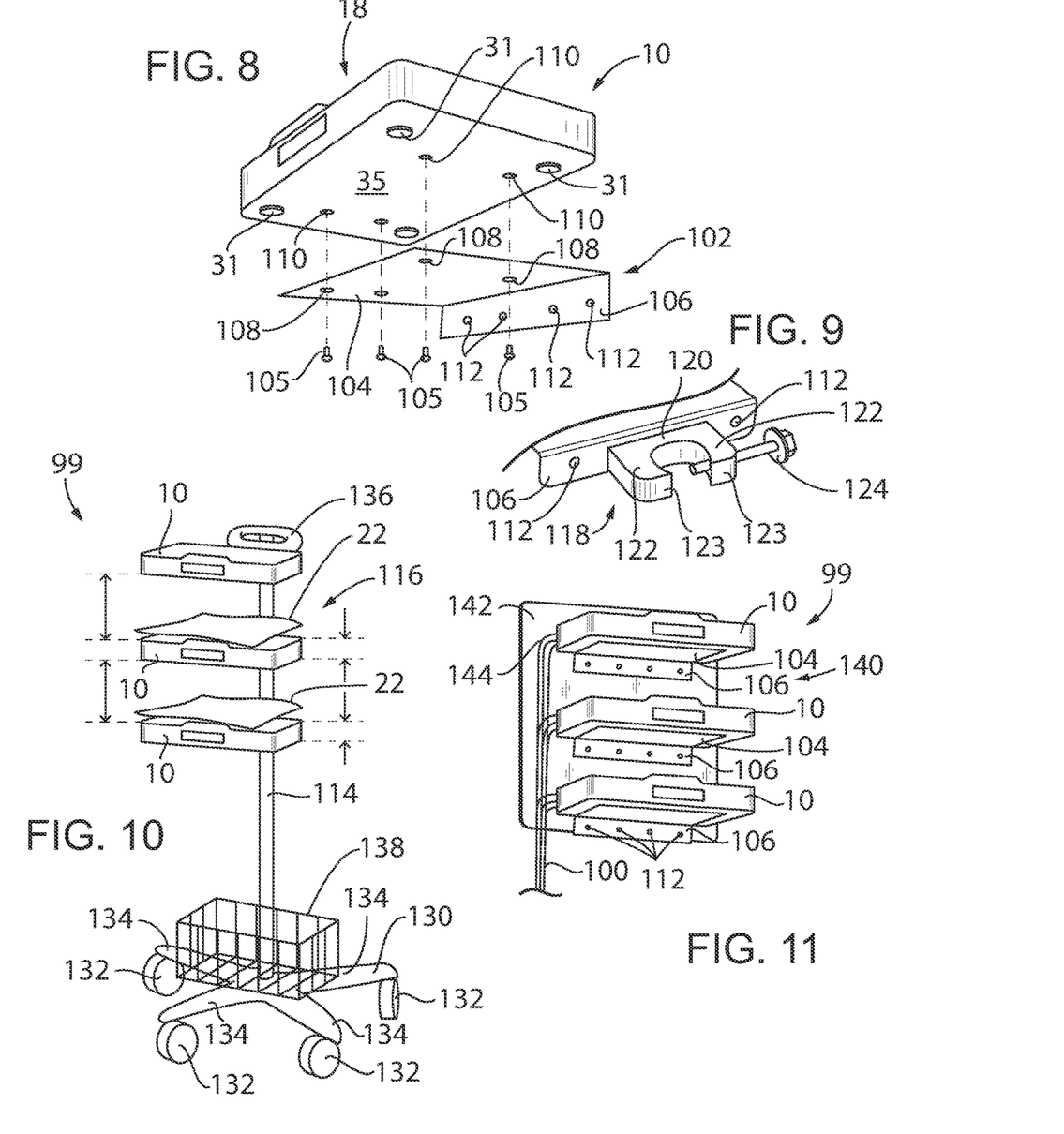
FIG. 8 is a front perspective view taken from below showing the attachment of the open plate to a mounting bracket.
FIG. 9 is a partial cutaway of the mounting bracket showing an attachment clamp attached to a rear wall of the mounting bracket.
FIG. 10 is a front perspective view taken from above of a rolling caster stand supporting a pole and allowing for portable movement of multiple warming modules attached to the pole in a vertically stacked configuration.
FIG. 11 is a front perspective view taken from below of a wall mount allowing multiple warming modules to be attached to the wall mount in a vertically stacked configuration.

The warming plate 12 may be held within the upper opening of the housing 18. The housing 30 may be fabricated of an injection molded polymer, thermoplastic or the like and may include a lower surface having downwardly extending feet 31 for support on a table or the like as seen in FIG. 8. The housing 30 may have vertically extending sidewalls 32 and vertically extending end walls 33 extending upward from a horizontally extending base wall 35 to the upper rim that remains open at its upper end to expose the upper surface of the warming plate 12 for receipt of the dialysis bag 22 onto the warming plate 12.

The upper rim 20 provides opposed sidewalls 16 and opposed end walls 17 sloping downwardly from a top of the upper rim 20 toward the warming plate 12 and contacting the warming plate 12 to provide a continuous watertight surface. The opposed sidewalls 16 and the opposed end walls 17 extend upwardly from the edges of the warming plate 12 by an angle less than 45 degree and approximately 10 to 45 degrees and approximately 35 to 45 degrees to provide an upper surface that is angled upward toward a dialysis bag 22 placed on the warming plate 12 as further described below.

A bottom edge of the downwardly extending opposed sidewalls 16 and opposed end walls 17 seal with the warming plate 12 using a L-shaped bracket 19 having a horizontal arm 21 supporting the underside of the warming plate 12 upward against the downwardly extending bottom edge of the downwardly opposed extending sidewalls 16 and opposed end walls 17, perpendicular to a vertical arm 25 extending upward and tightened into the upper rim 20. The vertical arm 25 of the L-shaped bracket 19 is screw tightened into the underside of the upper rim 20 to press the warming plate 12 upwards into the bottom edge of the downwardly extending opposed sidewalls 16 and opposed end walls 17. A suitable sealant 27 such as a rubber or a type of elastomeric material known in the art may be interposed between the warming plate 12 and opposed sidewalls 16 and opposed end walls 17 respectively to create a watertight seal.

Figure 4:
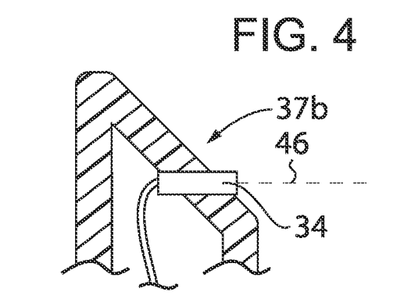
FIG. 4 is a fragmentary cross-section along line 4-4 of FIG. 2 of the front support platform supporting the light indicator.
Figure 5:
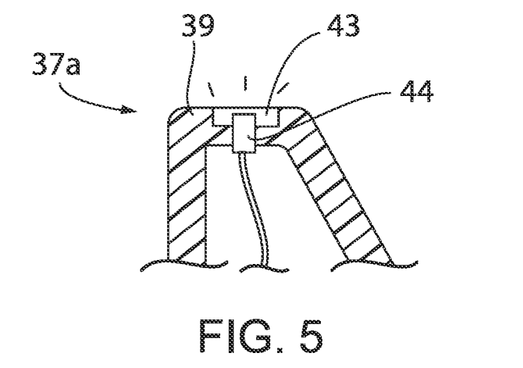
FIG. 5 is a fragmentary cross-section along line 5-5 of FIG. 2 of the rear support platform supporting a proximity sensor.

A central region of the opposed sidewalls 16 may include front and rear upwardly extending support platforms 37a, 37b. The front support platform 37a presents a substantially planar upper edge 39 extending parallel to the warming plate 12, and the rear support platform 37b presents a substantially planar inner edge 41 facing toward the warming plate 12. The inner edge 41 of rear support platform 37b may be substantially vertical or angled slightly upward toward the warming plate 12 between 10 to 30 degrees. The support platforms 37a, 37b are elevated above the opposed sidewalls 16 to carry the proximity sensor and indicator elements as will be described below. The support platforms 37a, 37b may extend along a length of the opposed sidewalls 16 approximately 10 to 20 cm or about ¼ to ⅓ a length of the opposed sidewalls 16.

A length of the opposed sidewalls 16 may be about 30 to 40 cm and at least 30 cm, and a width of the opposed end walls 17 may be about 20 to 30 cm and at least 20 cm. A height of the opposed sidewalls 16 and the opposed end walls 17 is less than 10 cm and preferably less than 5 cm to provide a low profile housing for efficient vertical stacking.

A height of the upper rim 20 above the warming plate 12 may be less than 2 cm and preferable less than 1 cm to provide a low rim that prevents the edges of the dialysis bag 22 from lifting off the warming plate 12 when placed thereon and maximizing contact of the dialysis bag 22 on the warming plate 12.

Referring to FIGS. 1, 2 and 4, the upper rim 20 may support at least one proximity sensor 34 indicating a presence of the dialysis bag 22 that may require heating. The at least one proximity sensor 34 may be optical switches, capacitive sensors, magnetic switches, or other proximity sensors known in the art providing an electrical signal that may communicate with the controller board 36 held within the housing 30.

In one embodiment of the present invention, the proximity sensors 34 are a pair of infrared proximity sensors 34 supported by the raised inner edge 41 of the rear support platform 37b extending along the vertically extending sidewall 32 and having an axis of sensitivity 46 directed inwardly and substantially parallel to the warming plate 12 toward the supported dialysis bag 22 across a width of the warming plate 12. It is understood that the proximity sensors 34 may alternatively be positioned along the vertically extending end wall 32 and have an axis of sensitivity 46 directed inwardly and substantially parallel to the warming plate 12 toward the supported dialysis bag 22 across a length of the warming plate 12 in a similar manner. The use of more than one proximity sensors 34 ensures that failure of one of the proximity sensor 34 will still allow the warming plate 12 to be activated.

The pair of infrared proximity sensors 34 may be displaced laterally, for example, approximately 10 to 20 cm apart or at least 10 cm apart so as to detect an alignment of the dialysis bag 22 on the warming plate 12. For example, if one of the infrared proximity sensors 34 does not detect the dialysis bag 22, this suggest that the bag is not properly aligned on the upper surface of the warming plate 12 for example if the dialysis bag 22 has shifted off the warming plate 12. The user will be alerted to this misalignment, for example, by a fault indicator described below, so that the misalignment can be corrected.

The infrared proximity sensors 34 detect changes in the reflected infrared light caused by the presence of the dialysis bag 22. This non-mechanical sensing system provides for robust and positive identification of both the placement and alignment of a dialysis bag 22 on the warming plate 12 in contrast, for example, to mechanical sensors which may detect a weight of the dialysis bag 22 on the warming plate 12 but not the alignment of the dialysis bag 22 on the warming plate 12.

The controller board 36 may communicate with the heater 28 so that the heater 28 may be activated only when a dialysis bag 22 is detected as present on the warming plate 12. Detection of the dialysis bag 22 may be detected by just one proximity sensor 34 or require that all proximity sensors 34 detect the dialysis bag 22 (to detect alignment).

Referring to FIGS. 1 and 2, the controller board 36 may also communicate with a temperature sensor pair 38 positioned approximately in the center of the warming plate 12 to be near a center region of the liquid 23 contained in the dialysis bag 22. This location provides a good measure of the average temperature of the liquid 23 in the dialysis bag 22. The temperature sensor pair 38 may be mounted on a heat collector plate 40 that projects upward from a plane of the warming plate 12 to provide a mesa-form pushing upward slightly on the lower sheet 24 into the dialysis bag 22 to ensure good contact therewith without substantially decreasing the thermal contact between the dialysis bag 22 and the warming plate 12 of the warming plate 12. The heat collector plate 40 and temperature sensor pair 38 are thermally isolated from the heater 28 and the warming plate 12 by means of this offset and an aperture cut in the heater 28 and warming plate 12 and separated from the heat collector plate 40 by a thermally insulating spacer ring 42.

Referring to FIGS. 2, 3, and 5, the controller board 36 may communicate with a light indicator 44 supported by the upper surface of the housing 30 beneath a light diffuser 43 spreading the light from the light indicators 44 across a larger area. The light indicators 44 may extend upwardly into the light diffuser 43 to indicate a warming state of the dialysis bag 22 as detected by the temperature sensor pair 38. The light indicators 44 may be light emitting diodes (LED) spaced beneath the light diffuser 43.

Turning to FIG. 5, the light diffuser 43 and LEDs 44 may be arranged on the planar upper edge 39 of the front support platform 37a which is unobstructed by the dialysis bag 22 and may be viewed directly by the user. The light diffuser 43 and LEDs 44 may also be arranged anywhere on an outer surface of the housing 30 in a similar manner to provide a quick visual indication to the user.

Referring now to FIGS. 2 and 3, in one embodiment, the light diffuser 43 may extend around a perimeter of the opening of the housing 30 on the upwardly sloping opposed sidewalls 16 and opposed end walls 17. The light emitted from the light diffuser 43 and LEDs 44 is directed upward and into the dialysis bag 22 so that the LEDs 44 illuminate the dialysis bag 22. The ends of the dialysis bag 22 may partially or fully overlie the upper rim 20 so that the light from the LEDs 44 is directed straight into the dialysis bag 22 to further illuminate the dialysis bag 22.

The illumination of the dialysis bag 22 turns the dialysis bag 22 into a large area indicator that glows when the LEDs 44 are activated. This arrangement provides a signaling device that is easily visible due to the large size of the dialysis bag 22 and clearly indicates the dialysis bag 22 associated with the signal by superimposing the signal on the relevant dialysis bag 22.

The LEDs 44 may be modulated to indicate the state of the dialysis bag 22 for example as warming, being fully warmed, or being over warmed. For example, a first intensity modulation may indicate that the dialysis bag 22 is warming and a steady illumination may indicate that the dialysis bag 22 is fully warmed. The intensity modulation may vary to indicate the progression of warming for example a second intensity modulation at a frequency higher than the first intensity modulation may indicate that the warming is closer to completion.

In another example, the LEDs 44 may emit light at different wavelengths to provide different colors indicating various states of the dialysis bag 22 in a similar manner. For example, a yellow or orange light may indicate that the dialysis bag 22 is warming, a green light may indicate that the dialysis bag 22 is fully warmed, and a red light may indicate that the dialysis bag 22 is over warmed.

Referring now to FIG. 1, an outer front surface of the housing 30 may provide for a control panel 60 having an alphanumeric display 62, for example, displaying a current temperature of the infusion liquid 23 or desired set point of the infusion liquid 23, a power switch 64 for turning the device on and off, a fault indicator 66 indicating that a problem has occurred, and a mode switch 68 to switch the display 62 between the current temperature of the infusion liquid 23, a desired set point of the infusion liquid, and a bag age. The switches 64, 68 may, for example, be membrane switches of a type known in the art and the ready indicator a light emitting diode.

Figure 6:
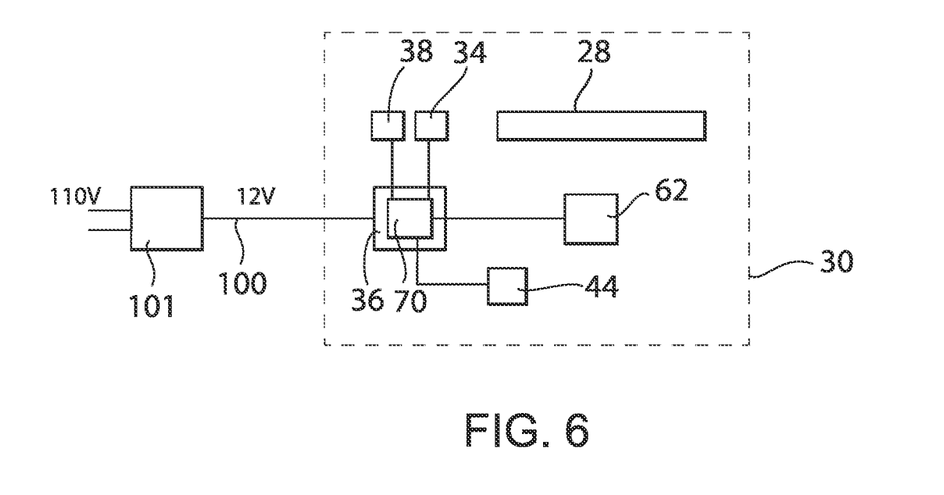
FIG. 6 is a schematic showing a remote wall adapter providing 12 V to a controller of the housing communicating with a heater, a temperature sensor, a light indicator, a proximity sensor, and a display.
Figure 7:
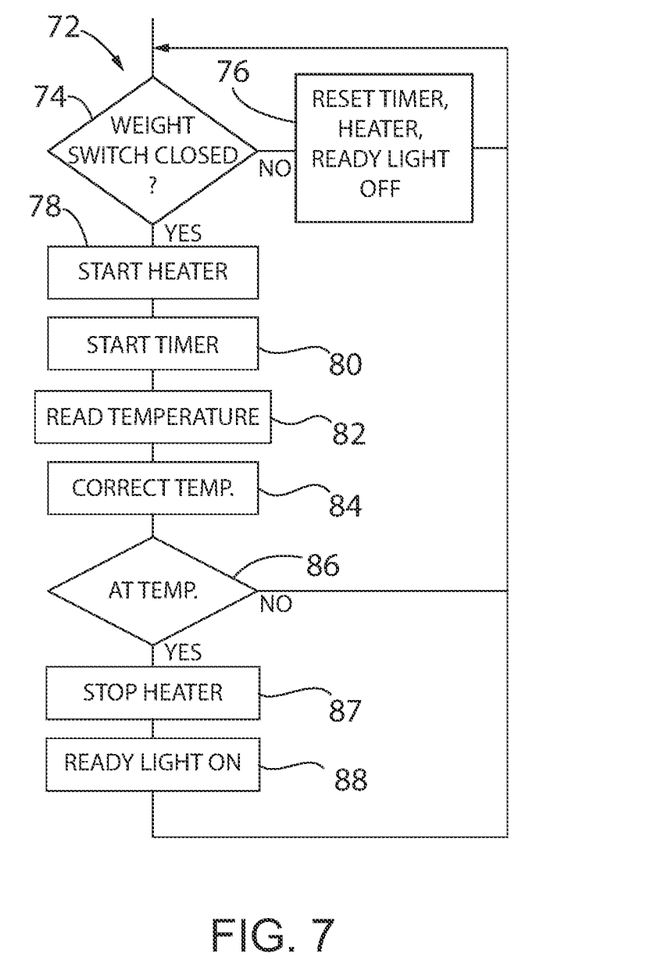
FIG. 7 is a flowchart of a program that may be executed by a controller board of the warming system.

Referring now to FIGS. 3, 6 and 7, the controller board 36 may include a microcontroller 70 or similar processor of a type well known in the art and including generally a processor, memory and various I/O circuits. The microcontroller 70 may receive signals from the thermal sensor pair 38 and the proximity sensors 34 and may provide control signals to the display 62, the light indicators 44 and the heater 28.

An internal program 72 executed by the microcontroller 70, as indicated by decision block 74, may first detect whether a dialysis bag 22 is in place on the warming plate 12 (as shown in FIG. 2) using the signal from the proximity sensors 34. If not, an internal timer used for determining the age of the dialysis bag 22 (with respect to how long it has been heated) is reset, and the light indicators 44 and the heater 28 are turned off (if they are on) as indicated by process block 76.

If a dialysis bag 22 is in place, the heater 28 may be turned on as indicated by process block 78, for example, by means of solid-state switches on the controller board 36 as controlled by the microcontroller 70. At this time a bag age timer is started as indicated by process block 80 that will keep track of how long the dialysis bag 22 has been in place and heated. The light indicators 44 are illuminated to indicate the bag age by changing the intensity modulation or color of the light indicators 44.

At process block 82, the temperature of the temperature sensor pair 38 is read and the separate temperature readings compared to see if they are beyond the predetermined range indicating an error at process block 84. If an error is indicated the heater may be turned off and in error indicated by fault indicator 66, otherwise the temperature values are averaged and this temperature is corrected for an empirically determined temperature offset representing a difference between the temperature of the contained liquid 23 and the temperature at the sensor pair 38 caused by the thermal resistance therebetween. This temperature difference will generally be added to the temperature read at the temperature sensor pair 38 at process block 84.

At decision block 86, a determination is made to see whether the temperature of the contained liquid 23 within the dialysis bag 22 is at a desired setpoint, the latter which may be entered by the user through the control panel 60 by conventional data entry routines not shown. This comparison considers the temperature at the temperature sensor pair 38 as corrected by the temperature offset described above. The range of set points entered by the user may be limited to those representing a safe range for the infusion liquid 23.

If at decision block 86 the deduced temperature of the infusion liquid 23 is below a predetermined range with respect to the desired setpoint, the program 72 loops back to decision block 74, otherwise the program proceeds to process block 87 and the heater is turned off and the light indicators 44 illuminated indicating that proper temperature has been obtained per process block 88.

At any time during this process, the mode switch 68 may be activated to allow the user to switch display 62 between the temperature of the contained liquid 23, the desired setpoint and the bag age. The temperature of the contained liquid 23 is corrected with the temperature offset as described above.

Referring to FIGS. 1 and 6, the controller board 36 may receive power from a line cord 100 passing into the housing 30 from a remote wall adapter 101 providing a voltage less than or equal to 12 V to the heater 28 from the remote wall adapter 101 through the line cord 100.

Referring now to FIG. 8, each warming unit 10 may be included as a modular unit of a multi-unit warming system 99 by attaching the lower surface of the housing 18 to a support mounting bracket 102. The mounting bracket 102 may be fabricated of a metal sheet or the like and may include a horizontal plate 104 supporting the housing 18 on its upper surface and a rear mounting plate 106 extending downwardly from a rear edge of the horizontal plate 104 to provide attachment of the mounting bracket 102 to a wall, pole or other support structure known in the art.

The housing 18 may be attached to the horizontal plate 104 by inserting screws 105 through holes 108 extending through the horizontal plate 104 into the corresponding screw holes 110 spaced apart on the lower surface of base wall 35 of the housing 18. The rear mounting plate 106 also includes holes 112 spaced apart along a length of the rear mounting plate 106 and allowing the mounting bracket 102 to be screw attached to a support structure for example as described below.

Referring also to FIGS. 9 and 10, multiple warming units 10 may be attached to a vertically extending pole 114 of a rolling caster stand 116 by using a clamp 118 attached to the rear mounting plate 106 of the mounting bracket 102. The clamp 118 may be attached to the rear mounting plate 106 for example using screws extending through holes 112 of the rear mounting plate 106 into screw holes at the rear of the clamp 118.

The clamp 118 may provide a C-shaped housing 120 having opposed arms 122 curved toward each other to provide a circular opening with open ends 123 spaced apart to receive the vertically extending pole 114 therein. The vertically extending pole 114 is secured by a tightening screw 124 extending across and through the open ends 123 of the opposed arms 122 to enclose the space between the opposed arms 122 and to tighten the opposed arms around the vertically extending pole 114.

The rolling caster stand 116 may include a rolling base 130 having downwardly extending casters 132 for rolling the caster stand 116 on the ground. The casters 132 may be separated on symmetric outwardly extending spider arms 134 of the rolling base 130 to provide balanced and broad ground support. The rolling base 130 may support the vertically extending pole 114 extending upwardly from a center of the rolling base 130 and terminating at an upper end which may include a handle 136 to facilitate rolling and maneuvering of the rolling caster stand 116 on the ground. The rolling caster stand 116 may also support other accessories for example held within a basket 138 carried by the rolling base 130.

The vertically extending pole 114 may support multiple warming units 10 in a vertically stacked configuration along the vertically extending pole 114. Each of the warming units 10 provides a low vertical profile for example the height of each warming unit 10 may be less than 10 cm and preferably less than 5 cm. The warming units 10 may be stacked to provide 10 to 20 cm and preferably less than 15 cm between each warming unit 10 or approximately less than 2 to 4 times the height of the dialysis bag 22 repose on the warming plate 12 to allow the dialysis bag 22 to be inserted and placed onto the warming plate 12 between warming units 10 while also conserving vertical space along the vertically extending pole 114. The height of each dialysis bag 22 when lying on the warming plate 12 may be less than 10 cm and typically less than 5 cm. In this arrangement multiple warming units 10 may be supported by the vertically extending pole 114 while conserving vertical space between each modular warming unit 10.

A weight of each warming unit 10 is also minimize to allow the rolling caster stand 116 to support multiple modular warming units 10 for example each warming unit 10 weighing less than 5 pounds and preferably less than 3 pounds. The rolling caster stand 116 may support 3 to 6 warming units 10 and at least three warming units 10.

Referring to FIGS. 8 and 11, in another embodiment, the multiple warming units 10 may also be attached to a wall unit 140 providing a vertical rear panel 142 having screw holes allowing the rear mounting plate 106 of the mounting bracket 102 to be attached to the rear panel 142 by screws extending through holes 112 of the mounting plate 106 into screw holes (not shown) of the rear panel 142. The screw holes may be spaced on the rear panel to allow for a space between the multiple warming units 10 to be about 10 to 20 cm and preferably less than 15 cm apart or approximately less than 2 to 4 times the height of the dialysis bag 22 repose on the warming plate 12 to allow the dialysis bag 22 to be inserted and placed onto the warming plate 12 between warming units 10 while still conserving vertical space. The wall unit 140 may support 3 to 6 warming units 10 and at least three warming units 10.

The rear panel 142 may further support longitudinal grooves 144 providing elongated depressions extending along the rear panel 142. The support grooves 144 may receive the line cord 100 of each warming unit 10 to allow the line cord 100 to pass from a rear of the housing 30 generally abutting the rear panel 142 to an outer edge of the rear panel 142. The grooves 144 may extend for example from top to bottom of the rear panel 142 along lateral edges of the mounted warming units 10 to pass the line cord 100 from the warming unit 10 to a bottom of the rear panel 142. A front open surface of the grooves 144, and the line cords 100 therein, may be concealed by a plastic cover extending over the grooves 144.

The light indicators 44 of the multi-unit warming system 99 provides a signaling device that clearly indicates the dialysis bag 22 associated with the signal by superimposing the signal on the relevant dialysis bag 22. In this respect, the light indicators 44 provide quick identification of warming state for the multiple dialysis bags 22 of the warming system 99.

Ideally the upper surface of the warming plate 12 will be substantially bare to provide improved thermal conductivity; however, it will be understood that a thin protective layer of plastic materials and/or anodization may be provided on the surface without unduly decreasing the effectiveness of the device. By providing a broad area, low-temperature heating of a substantially flattened dialysis bag 22, rapid and accurate temperature control of the contained liquid 23 may be effected.

Certain terminology is used herein for purposes of reference only, and thus is not intended to be limiting. For example, terms such as "upper", "lower", "above", "below", "clockwise", and "counterclockwise" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to a controller, computer or processor or its equivalent can be understood to include one or more computational devices including microprocessors, field programmable gate arrays, and application specific integrated circuits that can implement state aware logic and that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

We claim:

1. A warming module for infusible liquids comprising:
an upwardly exposed planar metal warming plate sized to receive a flexible polymer bag holding the infusible liquid;
a polymer housing supporting the warming plate and providing an upwardly extending peripheral rim presenting a sealed continuous surface between the housing and the warming plate wherein the rim is continuous around a periphery of the warming plate and has a height less than 2 cm and an angle of less than 45 degrees with respect to the warming plate;
a heater element attached to the warming plate to conduct heat through the warming plate and bag into the contained infusible liquid when the bag is held on the warming plate; and
at least one light indicator comprising a light diffuser indicating a warming state of the flexible polymer bag holding the infusible liquid wherein the at least one light indicator is positioned to at least partially underlie and directly contact the flexible polymer bag to direct light into the flexible polymer bag;
wherein the flexible polymer bag extends above the rim permitting the warming state of the flexible polymer bag to be seen at a horizontal line of sight above the rim.

2. The warming module of claim 1 wherein the heater element is attached to cover at least 90% of the warming plate area.

3. The warming module of claim 1 wherein the heater element includes heater control circuitry and a remote wall adapter providing a voltage less than or equal to 12 V to the heater and heater control circuitry from the remote wall adapter through an adapter cord.

4. The warming module of claim 1 wherein the warming module is less than five pounds.

5. The warming module of claim 1 wherein the rim includes at least one proximity sensor detecting the presence of the bag on the plate to control the heater.

6. The warming module of claim 5 wherein the at least one proximity sensor includes at least two proximity sensors that are displaced laterally from each other.

7. The warming module of claim 6 wherein the at least two proximity sensors are displaced apart by at least 10 cm.

8. The warming module of claim 5 wherein the at least one proximity sensor is an infrared sensor.

9. The warming module of claim 1 wherein the at least one light indicator is supported by an inner surface of the rim.

10. The warming module of claim 9 wherein the at least one light indicator is at least one light emitting diode bulb positioned beneath a light diffuser.

11. The warming module of claim 10 wherein the at least one light emitting diode bulb and light diffuser are arranged around a perimeter of the housing.

12. The warming module of claim 11 wherein the at least one light emitting diode bulb and light diffuser are arranged on the upwardly extending peripheral rim.

13. The warming module of claim 9 wherein the at least one light indicator presents a warming state indicating that the bag is warming and is not at a predetermined temperature or is warmed to a predetermined temperature by means of a first color indicating that the bag is warming and a second color indicating that the bag is warmed to the predetermined temperature.

14. The warming module of claim 9 wherein the at least one light indicator presents a warming state indicating that the bag is warming and is not at a predetermined temperature or is warmed to a predetermined temperature by means of changing an intensity of the light.

15. A warming system for infusible liquids comprising:
at least two warming modules arranged in a stacked configuration along an axis extending along a height of each warming module, each warming module having
an upwardly exposed planar metal warming plate sized to receive a flexible polymer bag holding the infusible liquid;
a polymer housing supporting the warming plate and providing an upwardly extending peripheral rim presenting a sealed continuous surface between the housing and the warming plate wherein the rim is continuous around a periphery of the warming plate and has a height less than 2 cm and an angle of less than 45 degrees with respect to the warming plate;
a heater element attached to the warming plate to conduct heat through the warming plate and bag into the contained infusible liquid when the bag is held on the warming plate;

at least one light indicator comprising a light diffuser indicating a warming state of the flexible polymer bag holding the infusible liquid wherein the at least one light indicator is positioned to at least partially underlie and directly contact the flexible polymer bag to direct light into the flexible polymer bag;

wherein the flexible polymer bag extends above the rim permitting the warming state of the flexible polymer bag to be seen at a horizontal line of sight above the rim.

16. The warming system of claim 15 further including a mounting bracket having a first plate configured to be attached to the housing and a second plate extending perpendicular to the first plate and configured to be attached to a support element.

17. The warming system of claim 15 wherein a spacing between the at least two warming modules is less than 15 cm.

18. The warming system of claim 15 wherein a spacing between the at least two warming modules is less than two times a height of the bag when reposed on the warming plate.

19. The warming system of claim 15 wherein the at least one light indicator is supported by an inner surface of the rim.

20. The warming system of claim 15 wherein the at least one light indicator is at least one light emitting diode bulb positioned beneath a light diffuser.

* * * * *